United States Patent
Fan

(10) Patent No.: US 11,549,114 B2
(45) Date of Patent: Jan. 10, 2023

(54) MULTIPLE RAPID DETECTION KITS AND METHODS FOR VARIOUS VIRUSES

(71) Applicant: APOLLO BIOMEDICAL, LLC, North Sale Lake, UT (US)

(72) Inventor: Chunlei Fan, HangZhou (CN)

(73) Assignee: Apollo Biomedical, LLC, North Sale Lake, UT (US)

( * ) Notice: Subject to any disclaimer, the term of this patent is extended or adjusted under 35 U.S.C. 154(b) by 0 days.

(21) Appl. No.: 16/942,666

(22) Filed: Jul. 29, 2020

(65) Prior Publication Data

US 2021/0301295 A1    Sep. 30, 2021

Related U.S. Application Data

(60) Provisional application No. 63/050,717, filed on Jul. 10, 2020, provisional application No. 63/050,722, filed on Jul. 10, 2020.

(51) Int. Cl.
| | |
|---|---|
| *C12N 15/62* | (2006.01) |
| *G01N 33/487* | (2006.01) |
| *G01N 1/34* | (2006.01) |
| *C07K 1/22* | (2006.01) |
| *C12P 19/34* | (2006.01) |
| *C12N 15/115* | (2010.01) |
| *C07K 14/47* | (2006.01) |

(52) U.S. Cl.
CPC .............. *C12N 15/62* (2013.01); *C07K 1/22* (2013.01); *C07K 14/47* (2013.01); *C12N 15/115* (2013.01); *C12P 19/34* (2013.01); *G01N 1/34* (2013.01); *G01N 33/48735* (2013.01); *C07K 2319/21* (2013.01); *C07K 2319/30* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 2003/0165970 A1* | 9/2003 | Hu | G01N 33/5761 435/6.16 |
| 2007/0212682 A1* | 9/2007 | Yu | G01N 33/56983 435/5 |
| 2010/0112547 A1* | 5/2010 | Lu | C07K 5/1019 435/5 |
| 2018/0372755 A1* | 12/2018 | Gehrke | G01N 33/6854 |
| 2021/0325388 A1* | 10/2021 | Ye | G01N 33/54387 |
| 2021/0389318 A1* | 12/2021 | Reed | G01N 33/54346 |

FOREIGN PATENT DOCUMENTS

WO   WO 2016/101075   *   6/2016   ............. G01N 33/53

OTHER PUBLICATIONS

Park et al."High urinary ACE2 concentrations are associated with severity of glucose intolerance and microalbuminuria", European Journal of Endocrinology 168: 203-210 (2013). (Year: 2013).*
'Abbots' Fast, $5, 15-Minute, Easy-to-Use COVID-19 Antigen Test Receives FDA Emergency Use Authorization; Mobile App Displays test Results to Help Our Return to Daily Life; Ramping Production to 50 Million Tests a Month Abbott Park, Ill., Aug. 26, 2020 PR Newswire.
Mews Medical "Avacta appoints COVID-19 rapid antigen test manufacturing partner" Avacta Group plc Aug. 12, 2020.
Becton, Dickinson and Company BD "Veritor(tm) System For Rapid Detection of SARS-CoV-2" Aug. 2020. Kit configured for testing nasal swab sample freshly collection, processed and dispensed directly onto assay test device.
Quidel "Sofia SARS Antigen FIA" Jul. 2020 quidel.com.

* cited by examiner

*Primary Examiner* — Anand U Desai
(74) *Attorney, Agent, or Firm* — Holland & Hart LLP

(57) ABSTRACT

Novel Coronavirus/MERS-CoV/Influenza Virus A/B Multiple Rapid Detection Kit is disclosed. The kit has the advantages of high sensitivity, good specificity, high speed (3-15 minutes), simplicity and low cost.

21 Claims, 3 Drawing Sheets
(3 of 3 Drawing Sheet(s) Filed in Color)

Specification includes a Sequence Listing.

SEQUENCE LISTING

```
<160> NUMBER OF SEQ ID NOS: 5

<210> SEQ ID NO 1
<211> LENGTH: 2324
<212> TYPE: DNA
<213> ORGANISM: Artificial Sequence
<220> FEATURE:
<223> OTHER INFORMATION: Synthetic Construct

<400> SEQUENCE: 1
gaattcatga gcagcagcag ctggctgctg ctgagcctgg tggccgtgac cgccgctcag       60
tccaccatcg aggagcaggc caagaccttc ctggacaagt tcaatcacga ggccgaggac      120
ctgttttacc agagcagcct ggcctcctgg aactacaaca ccaatatcac cgaggagaac      180
gtgcagaaca tgaataacgc cggcgataag tggagcgcct tcctgaagga gcagagcacc      240
ctggcccaga tgtacccccct gcaggagatc cagaacctga ccgtgaagct gcagctgcag      300
gccctgcagc agaatggctc cagcgtgctg agcgaggata agtccaagag actgaatacc      360
atcctgaata ccatgtccac catctactcc accggcaagg tgtgcaatcc tgacaatcct      420
caggagtgtc tgctgctgga gcccggcctg aacgagatca tggccaacag cctggattac      480
aatgagaggc tgtgggcctg ggagtcctgg aggagcgagg tgggcaagca gctgaggcct      540
ctgtacgagg agtacgtggt gctgaagaac gagatggcca gggccaacca ctacgaggat      600
tacggcgatt actggagggg cgattacgag gtgaatggcg tggatggcta cgattactcc      660
agaggccagc tgatcgagga tgtggagcac accttcgagg agatcaagcc tctgtacgaa      720
cacctgcacg cctacgtgag agccaagctg atgaacgcct accctcctg catctccccc      780 atcggctgcc tgcctgccca cctgctgggc gatatgtggg gcagattctg gaccaatctg      840
tactccctga ccgtgccttt cggccagaag cccaatatcg atgtgaccga cgccatggtg      900
gatcaggcct gggacgccca gagaatcttt aaggaggccg agaagttctt tgtgtccgtg      960
ggcctgccca atatgaccca gggcttctgg gagaatagca tgctgaccga ccctggcaat     1020
gtgcagaagg ccgtgtgcca ccccaccgcc tgggacctgg gaaagggcga ctttagaatc     1080
ctgatgtgca ccaaggtgac catggatgac ttcctgaccg cccaccacga gatgggccac     1140
atccagtacg acatggccta cgccgcccag ccccttcctgc tgaggaatgg cgccaatgag     1200
ggcttccacg aggccgtggg cgagatcatg tccctgtccg ccgccacccc caagcacctg     1260
aagagcatcg gcctgctgag ccctgatttt caggaggaca atgagacaga gatcaacttt     1320
ctgctgaagc aggccctgac catcgtgggc acctgccct tcacctacat gctggagaag     1380
tggaggtgga tggtgtttaa gggcgagatc cctaaggacc agtggatgaa gaagtggtgg     1440
```

-continued

```
gagatgaaga gagagatcgt gggcgtggtg gagcccgtgc cccacgatga gacatactgt    1500
gaccctgcct ccctgtttca cgtgtccaat gactacagct tcatcaggta ctacaccagg    1560
accctgtacc agtttcagtt ccaggaggcc ctgtgtcagg ccgccaagca cgagggcccc    1620
ctgcataagt gtgatatcag caactccacc gaggccggcc agaagctgtt taatatgctg    1680
aggctgggca agagcgagcc ctggaccctg ccctggaga acgtggtggg cgccaagaat    1740
atgaacgtga ggcccctgct gaactacttt gagcccctgt tcacctggct gaaggaccag    1800
aacaagaact cctttgtggg ctggagcacc gactggtccc cctacgccga ccagagcatc    1860
aaggtgagga tctccctgaa gtccgccctg ggcgatagag cctacgagtg gaacgataac    1920
gagatgtacc tgttcaggag ctccgtggcc tacgccatga ggcagtactt cctgaaggtg    1980
aagaatcaga tgatcctgtt cggcgaggag gatgtgaggg tggccaacct gaagcccaga    2040
atctccttca acttttttcgt gaccgccccc aagaacgtgt ccgacatcat ccctaggacc    2100
gaggtggaga aggccatcag aatgtccagg tccagaatca cgacgccttt cagactgaat    2160
gataacagcc tggagttcct gggcatccag cccacccctgg ccccccctaa ccagccacct    2220
gtgggcagcg gcggcagcgg cggaagcgct ggactgaacg atatcttcga ggcccagaag    2280
atcgagtggc acgagcatca ccatcaccat cattgagcgg ccgc                     2324
```

<210> SEQ ID NO 2
<211> LENGTH: 769
<212> TYPE: PRT
<213> ORGANISM: Artificial Sequence
<220> FEATURE:
<223> OTHER INFORMATION: Synthetic Construct

<400> SEQUENCE: 2

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205
```

-continued

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
        660                 665                 670

Ala Asn Leu Lys Pro Arg Ile Ser Phe Asn Phe Val Thr Ala Pro
    675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Gly Ser Gly Gly Ser Gly Ser Ala Gly Leu Asn Asp
        740                 745                 750

Ile Phe Glu Ala Gln Lys Ile Glu Trp His Glu His His His His
    755                 760                 765

His

<210> SEQ ID NO 3
<211> LENGTH: 2378
<212> TYPE: DNA
<213> ORGANISM: Artificial Sequence
<220> FEATURE:
<223> OTHER INFORMATION: Synthetic Construct

<400> SEQUENCE: 3

```
gaattcatgg ccgctgacag ccagaccccc tggctgctga ccttcagcct gctgtgtctg      60
ctgtggcccc aggaggccgg ggctcatcac catcaccatc atggcctgaa cgacatcttc     120
gaggcccaga gatcgagtg cacgaagga tccaacaagg caccgacga cgccaccgcc      180
gacagcagaa aaacatacac cctgaccgac tacctgaaga cacctacag actgaaactg     240
tacagcctga tggatcag cgaccacgaa tacctgtaca acaggaaaa caacatcctg      300
gtgttcaacg ccgagtacgg caacagcagc gtgttcctgg aaaacaacac cttcgacgag     360
ttcggccaca gcatcaacga ctacagcatc agccccgacg ccagttcat cctgctggag     420
tacaactacg tgaagcagtg gagacactcc tacaccgcca gctacgacat ctatgacctg     480
aataaaagac agctgattac cgaggagaga tcccccaaca cacccagtg ggtgacatgg     540
agcccagtgg ccacaagct ggcctacgtg tggaataacg acatctacgt gaagatcgaa     600
ccaaacctgc ccagctacag aatcacctgg accggcaagg aagacatcat ctacaacgga     660
atcaccgact gggtgtacga agaggaagtg ttcagcgcct acagcgccct gtggtggagc     720
cccaacggca ccttcctggc ctacgcccag ttcaacgaca cagaggtgcc cctgatcgag     780
tacagctttt atagcgacga aagcctgcag taccccaaga ccgtgagagt gcccctaccc     840
aaggccggcg ctgtgaaccc caccgtgaag ttctttgtgg tgaataccga cagcctgagc     900
tccgtgacca acgccaccag catccagatc accgccccg ccagcatgct gatcggcgac     960
cattatctgt gcgacgtgac ctgggccacc caggaaagaa tcagcctgca gtggctgcgc    1020
agaatccaga actacagcgt gatggacatc tgtgactacg acgagagcag cggagatgg    1080
aactgcctgg tggccagaca gcacatcgag atgagcacca caggctgggt gggcagattc    1140
agacccagcg agccacattt caccctggac ggaaacagct tttacaagat catcagcaac    1200
```

```
gaagagggct acagacacat ctgctatttc cagatcgaca aaaaggattg caccttcatc   1260
accaagggaa cctgggaggt gatcggaatc gaggccctga ccagcgacta cctgtactac   1320
attagtaacg aatacaaggg catgcccggc ggcagaaacc tgtacaagat ccagctgagc   1380
gactacacca aggtgacatg cctgagctgt gaactgaacc ccgaaagatg tcagtactac   1440
agcgtgagct tcagcaagga ggccaagtat taccagctga ggtgcagcgg ccccggactg   1500
cctctgtaca ccctgcacag cagcgtgaac gacaaaggcc tgagagtgct ggaggacaac   1560
agcgccctgg acaaaatgct gcagaacgtg cagatgccca gcaagaaact ggacttcatc   1620
atcctgaacg aaaccaagtt ttggtaccag atgattctgc cacccccactt cgacaaaagc   1680 aaaaagtatc ccctgctgct ggacgtgtac gccggcccat gctcccagaa agccgacacc   1740
gtgttcagac tgaactgggc cacctacctg gcctccaccg aaaacatcat cgtggccagc   1800
ttcgacggcc ggggcagcgg atatcaggga gacaaaatca tgcacgccat caatagaaga   1860 ctgggaaccct tcgaggtgga ggaccagatt gaggccgcca gacagttcag caaaatgggc   1920
tttgtggaca acaagaggat cgccatctgg ggctggagct acggagggta cgtgacatct   1980
atggtgctgg ggagtggaag cggcgtgttt aagtgtggaa tcgccgtggc ccccgtgtct   2040
agatgggagt actacgacag cgtgtacaca gagagatata tgggactgcc caccccgag   2100 gataatctgg accactacag aaatagcacc gtgatgagca gagccgaaaa cttcaagcag   2160
gtggagtacc tgctgatcca tggcaccgcc gacgacaacg tgcacttcca gcagagcgcc   2220
cagatcagca agccctggt ggacgtgggc gtggacttcc aggccatgtg gtacaccgat   2280
gaagaccacg gcatcgccag cagcaccgcc catcagcata tctacacccca catgtcccac   2340 ttcatcaagc agtgcttctc cctgccttga gcggccgc                          2378
```

<210> SEQ ID NO 4
<211> LENGTH: 761
<212> TYPE: PRT
<213> ORGANISM: Artificial Sequence
<220> FEATURE:
<223> OTHER INFORMATION: Synthetic Construct

<400> SEQUENCE: 4

```
His His His His His His Gly Leu Asn Asp Ile Phe Glu Ala Gln Lys
1               5                   10                  15

Ile Glu Trp His Glu Gly Ser Asn Lys Gly Thr Asp Asp Ala Thr Ala
            20                  25                  30

Asp Ser Arg Lys Thr Tyr Thr Leu Thr Asp Tyr Leu Lys Asn Thr Tyr
        35                  40                  45

Arg Leu Lys Leu Tyr Ser Leu Arg Trp Ile Ser Asp His Glu Tyr Leu
    50                  55                  60

Tyr Lys Gln Glu Asn Asn Ile Leu Val Phe Asn Ala Glu Tyr Gly Asn
65                  70                  75                  80

Ser Ser Val Phe Leu Glu Asn Asn Thr Phe Asp Glu Phe Gly His Ser
                85                  90                  95

Ile Asn Asp Tyr Ser Ile Ser Pro Asp Gly Gln Phe Ile Leu Leu Glu
            100                 105                 110

Tyr Asn Tyr Val Lys Gln Trp Arg His Ser Tyr Thr Ala Ser Tyr Asp
        115                 120                 125

Ile Tyr Asp Leu Asn Lys Arg Gln Leu Ile Thr Glu Glu Arg Ile Pro
    130                 135                 140

Asn Asn Thr Gln Trp Val Thr Trp Ser Pro Val Gly His Lys Leu Ala
145                 150                 155                 160
```

```
Tyr Val Trp Asn Asn Asp Ile Tyr Val Lys Ile Glu Pro Asn Leu Pro
                165                 170                 175

Ser Tyr Arg Ile Thr Trp Thr Gly Lys Glu Asp Ile Ile Tyr Asn Gly
            180                 185                 190

Ile Thr Asp Trp Val Tyr Glu Glu Val Phe Ser Ala Tyr Ser Ala
        195                 200                 205

Leu Trp Trp Ser Pro Asn Gly Thr Phe Leu Ala Tyr Ala Gln Phe Asn
        210                 215                 220

Asp Thr Glu Val Pro Leu Ile Glu Tyr Ser Phe Tyr Ser Asp Glu Ser
225                 230                 235                 240

Leu Gln Tyr Pro Lys Thr Val Arg Val Pro Tyr Pro Lys Ala Gly Ala
                245                 250                 255

Val Asn Pro Thr Val Lys Phe Phe Val Val Asn Thr Asp Ser Leu Ser
            260                 265                 270

Ser Val Thr Asn Ala Thr Ser Ile Gln Ile Thr Ala Pro Ala Ser Met
        275                 280                 285

Leu Ile Gly Asp His Tyr Leu Cys Asp Val Thr Trp Ala Thr Gln Glu
        290                 295                 300

Arg Ile Ser Leu Gln Trp Leu Arg Arg Ile Gln Asn Tyr Ser Val Met
305                 310                 315                 320

Asp Ile Cys Asp Tyr Asp Glu Ser Ser Gly Arg Trp Asn Cys Leu Val
                325                 330                 335

Ala Arg Gln His Ile Glu Met Ser Thr Thr Gly Trp Val Gly Arg Phe
            340                 345                 350

Arg Pro Ser Glu Pro His Phe Thr Leu Asp Gly Asn Ser Phe Tyr Lys
        355                 360                 365

Ile Ile Ser Asn Glu Glu Gly Tyr Arg His Ile Cys Tyr Phe Gln Ile
        370                 375                 380

Asp Lys Lys Asp Cys Thr Phe Ile Thr Lys Gly Thr Trp Glu Val Ile
385                 390                 395                 400

Gly Ile Glu Ala Leu Thr Ser Asp Tyr Leu Tyr Tyr Ile Ser Asn Glu
                405                 410                 415

Tyr Lys Gly Met Pro Gly Gly Arg Asn Leu Tyr Lys Ile Gln Leu Ser
            420                 425                 430

Asp Tyr Thr Lys Val Thr Cys Leu Ser Cys Glu Leu Asn Pro Glu Arg
        435                 440                 445

Cys Gln Tyr Tyr Ser Val Ser Phe Ser Lys Glu Ala Lys Tyr Tyr Gln
        450                 455                 460

Leu Arg Cys Ser Gly Pro Gly Leu Pro Leu Tyr Thr Leu His Ser Ser
465                 470                 475                 480

Val Asn Asp Lys Gly Leu Arg Val Leu Glu Asp Asn Ser Ala Leu Asp
                485                 490                 495

Lys Met Leu Gln Asn Val Gln Met Pro Ser Lys Lys Leu Asp Phe Ile
            500                 505                 510

Ile Leu Asn Glu Thr Lys Phe Trp Tyr Gln Met Ile Leu Pro Pro His
        515                 520                 525

Phe Asp Lys Ser Lys Lys Tyr Pro Leu Leu Leu Asp Val Tyr Ala Gly
        530                 535                 540

Pro Cys Ser Gln Lys Ala Asp Thr Val Phe Arg Leu Asn Trp Ala Thr
545                 550                 555                 560

Tyr Leu Ala Ser Thr Glu Asn Ile Ile Val Ala Ser Phe Asp Gly Arg
                565                 570                 575
```

```
Gly Ser Gly Tyr Gln Gly Asp Lys Ile Met His Ala Ile Asn Arg Arg
            580                 585                 590

Leu Gly Thr Phe Glu Val Glu Asp Gln Ile Glu Ala Ala Arg Gln Phe
        595                 600                 605

Ser Lys Met Gly Phe Val Asp Asn Lys Arg Ile Ala Ile Trp Gly Trp
        610                 615                 620

Ser Tyr Gly Gly Tyr Val Thr Ser Met Val Leu Gly Ser Gly Ser Gly
625                 630                 635                 640

Val Phe Lys Cys Gly Ile Ala Val Ala Pro Val Ser Arg Trp Glu Tyr
                645                 650                 655

Tyr Asp Ser Val Tyr Thr Glu Arg Tyr Met Gly Leu Pro Thr Pro Glu
            660                 665                 670

Asp Asn Leu Asp His Tyr Arg Asn Ser Thr Val Met Ser Arg Ala Glu
            675                 680                 685

Asn Phe Lys Gln Val Glu Tyr Leu Leu Ile His Gly Thr Ala Asp Asp
        690                 695                 700

Asn Val His Phe Gln Gln Ser Ala Gln Ile Ser Lys Ala Leu Val Asp
705                 710                 715                 720

Val Gly Val Asp Phe Gln Ala Met Trp Tyr Thr Asp Glu Asp His Gly
                725                 730                 735

Ile Ala Ser Ser Thr Ala His Gln His Ile Tyr Thr His Met Ser His
            740                 745                 750

Phe Ile Lys Gln Cys Phe Ser Leu Pro
        755                 760

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Gly Leu Asn Asp Ile Phe Glu Ala Gln Lys Ile Glu Trp His Glu
1               5                   10                  15
```

MULTIPLE RAPID DETECTION KITS AND METHODS FOR VARIOUS VIRUSES

RELATED APPLICATIONS

This application claims the benefit of U.S. Provisional Patent Application No. 63/050,717, filed Jul. 10, 2020, and U.S. Provisional Patent Application No. 63/050,722, filed Jul. 10, 2020, and PCT Application No. PCT/CN2020/081636, filed Mar. 27, 2020, and People's Republic of China national patent application to which PCT Application No. PCT/CN2020/081636 claims priority, filed Feb. 26, 2020, all such applications being hereby incorporated by reference herein in their entireties including, but not limited to, those portions that specifically appear hereinafter, this incorporation by reference being made with the following exception: In the event that any portion of the above-referenced applications are inconsistent with this present application, this present application supersedes said above-referenced provisional application.

STATEMENT REGARDING FEDERALLY SPONSORED RESEARCH OR DEVELOPMENT

Not Applicable.

REFERENCE TO SEQUENCE LISTING

The content of the ASCII text file of the sequence listing named "110279.0006 Sequence Listing_ST25" which was created on Feb. 18, 2021 and is 20,133 bytes in size submitted electronically via EFS-WEB with this U.S. Patent Application is incorporated by reference in its entirety.

BACKGROUND

1. The Field of the Present Disclosure

This disclosure is particularly directed towards the field of biotechnology. Specifically, this disclosure is directed towards systems and methods for virus detection.

2. Description of the Related Art

SARS-CoV-2 is the seventh coronavirus known to infect humans. The remaining six are HCoV-229E, HCoV-OC43, HCoV-NL63, HCoV-HKU1, SARS-CoV and MERS-CoV. Studies have shown that SARS-CoV-2, SARS-CoV and HCoV-NL63 infect humans through the interaction between the virus and ACE2 receptor on host cell membrane mediated by the virus spike glycoprotein (s-protein). Corona Virus Disease 2019 (COVID-19) is an acute respiratory infectious disease caused by novel coronavirus infection. The common symptoms are fever, accompanied by dry cough, fatigue, dyspnea and other symptoms. Some people may have headaches, dizziness and other symptoms, but some may not have particularly notable symptoms. MERS-CoV is a coronavirus of the genus C subgroup. After infection, it causes Middle East Respiratory Syndrome (MERS). Most cases of MERS virus infection occur in Middle East. Unlike SARS-COV-2, MERs-COV infects humans through the interaction of its envelope S-protein with the DPP4 receptor on the host cell membrane. Influenza is an acute respiratory tract infection caused by influenza virus. It is a disease with strong infectivity and fast transmission speed. Typical clinical symptoms are: acute high fever, systemic pain, significant fatigue and mild respiratory symptoms. General autumn and winter season is its high incidence, caused by complications and death phenomenon is very serious. The disease is caused by influenza virus, can be divided into A (A), B (B), C (C) three types, A virus often antigen variation, infectious, rapid spread, easy to occur in A wide range of epidemics.

Symptoms can be difficult to distinguish between COVID-19, MERS and influenza, and even some test kits have severe cross-reactions. Therefore, the development of a detection kit, even one which can be used at home, that can quickly distinguish COVID-19, MERS and influenza is of great significance for the global epidemic and epidemic surveillance of coronavirus and influenza viruses.

BRIEF SUMMARY

Illustrative embodiments may include a novel coronavirus/MERS-CoV/influenza virus AB multiple rapid detection kit. It is characterized in that the kit method contains ACE2 protein labeled with color latex, and the preparation method of ACE2 protein labeled with color latex includes the following steps:

1.1 The c-terminal of the human ACE2 gene was sequentially connected to AVI tag sequence and the 6×His tag to form an artificially designed sequence. The artificially designed sequence was optimized by the host cell codon and then subcloned into a vector under its CMV promoter. A plasmid expressing ACE2-AVI tag-6×His tag fusion protein was constructed, which is called ACE2 fusion protein plasmid.

1.2 Transfection of ACE2 fusion protein plasmid constructed in step1.1 into a cell line, and a stable transfected cell line expressing ACE2 fusion protein was established. Cultured and expanded the stable transfected cells, collected the supernatant which contained ACE2 fusion protein.

1.3 ACE2 fusion protein was obtained from the culture supernatant prepared in step1.2 by protein purification column that is His tag affinity column, such as Ni2+ or Co2+ column and ACE2 protein was obtained.

1.4 The ACE2 protein obtained in step1.3 was site-directed biotinylated at its c-terminal by the biotin-protein ligase BirA. And the ACE2-biotin was obtained 1.5 Streptavidin SA was coupled to color latex with carboxylic group, obtained L-SA; ACE2-biotin obtained in step1.4 was co-incubated with L-SA, the L-SB-ACE2 was obtained.

BRIEF DESCRIPTION OF THE DRAWINGS

This application/patent file contains at least one drawing executed in color. Copies of this patent or patent application publication with color drawing(s) will be provided by the Office upon request and payment of the necessary fee.

DETAILED DESCRIPTION

Figure 1:
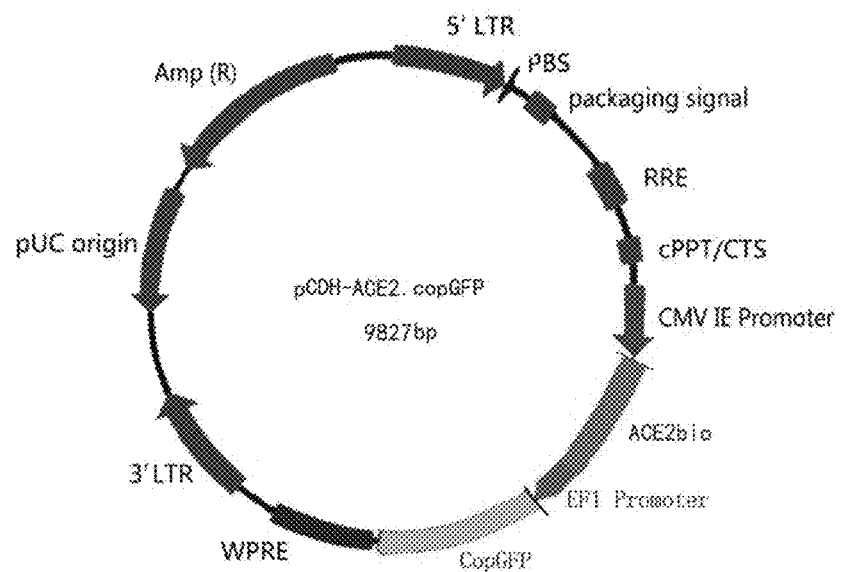
FIG. 1 is a plasmid map of pCDH-ACE2.copGFP.

Embodiments disclosed herein include devices and methods for novel coronavirus/MERS-CoV/influenza virus A/B multiple rapid detection kits. The embodiments disclosed herein may detect one or more viruses, as taught herein, including novel coronavirus/MERS-CoV/influenza virus A/B.

For the purposes of promoting an understanding of the principles in accordance with this disclosure, reference will now be made to the embodiments described herein and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the present rapid virus test kit is disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, un-recited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

The terms "weight percent," "percent by weight," and "% by weight" all refer to the concentration of a component substance as the weight of the component substance divided by the weight of the composition multiplied by 100. The weight percentages and quantitative terms referred to herein shall be considered to include the ranges 1-2, 2-3, 1-3 and all the values within. Thus, if the weight percentage is 10, this may include the values 7 and 13 and all the values between those.

In view of the above technical problems in existing technologies, a novel coronavirus/MERS-CoV/influenza virus AB multiple rapid detection kit is disclosed herein. Some embodiments may include two subunits, S1 and S2, in the spike protein of coronavirus, where the S1 subunit acts as a ligand to interact with a receptor on the human cell membrane to form a specific binding. The SARS-CoV-2 invades human cells by specifically binding of its S1 protein (ligand) to ACE2 receptor on human cellular membrane with a high affinity (KD measured as 15 nM, which is 10-20 times stronger than SARS-CoV). According to the immunochromatography principle of the sandwich method, the recombinant human ACE2 protein is used in some embodiments to replace one of the anti-s-protein monoclonal antibodies to be labeled with color latex and spray it on the release pad of the test strip.

In some embodiments, the SARS-CoV-2 test line on the test strip is coated with anti-S1 protein of SARS-CoV-2 polyclonal antibodies, which is used to capture SARS-CoV-2 and latex labeled ACE2 complex in the chromatography. If there is SARS-CoV-2 in the test sample, the T-line has the color latex agglutination. If no SARS-CoV-2 is present in the test sample, the color of T-line will not display color. The MERS-CoV invades human cells by specifically binding of its S1 protein (ligand) to DPP4 receptor on human cellular membrane. Similarly, in accordance with the illustrative embodiments, the recombinant human DPP4 protein is used to replace one of the anti-S1-protein monoclonal antibodies to be labeled with color latex and spray it on the release pad of the test strip. The MERS-CoV test line on the test strip may be coated with anti-S1 protein of MERS-CoV polyclonal antibodies, which may be used to capture MERS-CoV and latex labeled DPP4 complex in the chromatography. Embodiments may be configured such that if there is MERS-CoV in a test sample, the T-line has the color latex agglutination, and if no MERS-CoV is present in the test sample, the color of T-line will not display color.

Some illustrative embodiments may include an influenza A test. For influenza A test, the anti-influenza A virus monoclonal antibodies, anti-IFVA mAb (capture) may be labeled with color latex respectively, which may be sprayed on the release pad of the test strip. The influenza A test line on the test strip may be coated with anti-IFVA mAb (detection), which may be used to capture influenza A virus and latex anti-IFVA mAb (capture) complex in the chromatography. In some embodiments, during detection, if there is influenza A virus in the test sample, the T-line has the color latex agglutination. If no influenza A virus is present in the test sample, the color of T-line may not display color. A similar procedure may be used for testing for influenza B in some embodiments.

Figure 3:
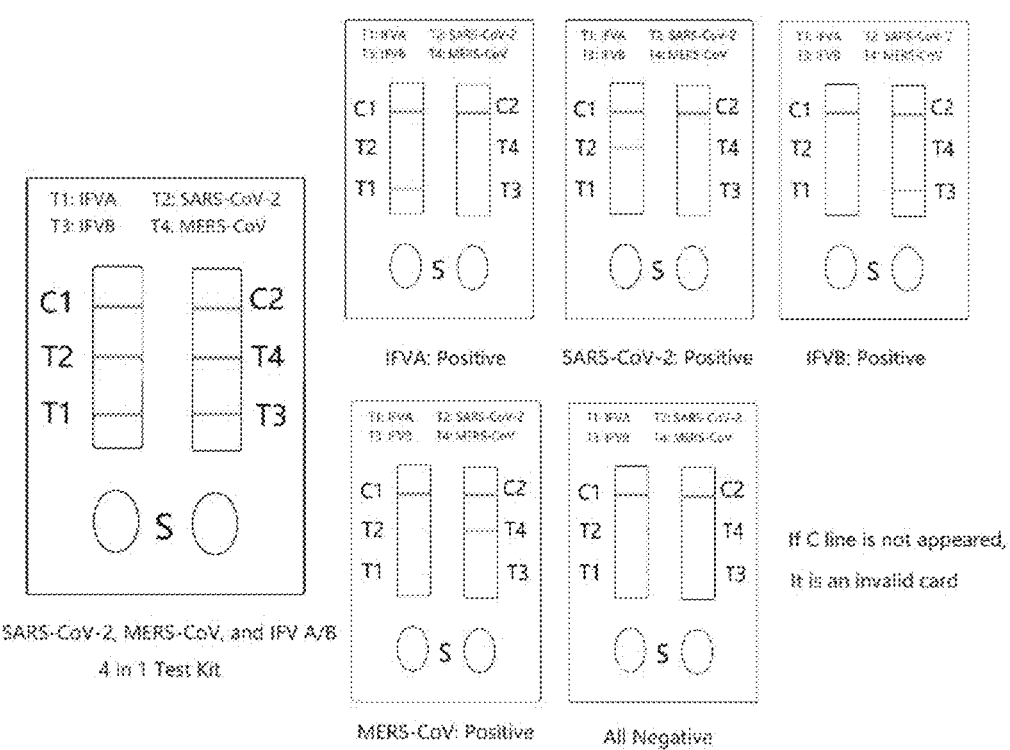
FIG. 3 depicts a schematic diagram of detection principle of SARS-CoV-2, MERS-CoV, influenza A and influenza B virus test kit, according to embodiments discussed herein.

In some illustrative embodiments, the test kit contains two test strips, see FIG. 3. In one of the test strips, on the nitrocellulose (NC) membrane, the anti-IFVA mAb (detection) may be coated at the test area (T1), the rabbit anti-S1 protein of novel coronavirus antibodies may be coated at the test area (T2), and the goat anti-rabbit IgG polyclonal antibody may be coated at the control area (C1). Latex-labeled ACE2 protein, Latex-labeled anti-IFVA mAb (capture) and Latex-labeled rabbit IgG may be embedded in the release pad. In the other strip, on the nitrocellulose (NC) membrane, the anti-IFVB mAb (detection) may be coated at the test area (T3), the rabbit anti-S1 protein of MERS-CoV antibodies may be coated at the test area (T4), and the goat anti-rabbit IgG polyclonal antibody may be coated at the control area (C2). Latex-labeled DPP4 protein, Latex-labeled anti-IFVB mAb (capture) and Latex-labeled rabbit IgG may be embedded in the release pad.

In some illustrative embodiments, the method of testing may include dropping a sample into a sample well. In other illustrative embodiments, the method may include adding about three drops of the sample, and the sample may laterally flow from the bottom to the top under the capillary effect. If the sample contains the SARS-CoV-2, the latex-labeled ACE2 protein may be bound by the S1 protein of virus, and then captured by anti-S1 protein antibodies coated on the test area (T2) and the T2 line may appear. If the sample does not contain the SARS-CoV-2, the latex-labeled ACE2 protein may not be captured by anti-S1 protein antibodies coated on the test area (T2), therefore, no T2 line may appear.

In some illustrative embodiments, if the sample does not contain influenza A virus, the latex-labeled influenza A monoclonal antibody may not be captured and bound by the influenza A monoclonal antibody coated on the test area (T1) during the chromatography process, and the T1 area will not be out of a line. If the sample contains influenza A virus, the latex-labeled influenza A monoclonal antibody may be first bound by the influenza A virus in the sample. During the chromatography process, it may then combined with the influenza A monoclonal antibody may coat on the T1 area, and a colored line may appear in the T1 area.

If the sample does not contain influenza B virus, the latex labeled influenza B monoclonal antibody may not be captured and bound by the influenza B monoclonal antibody coated on the test area (T3) during the chromatography process, and the T3 area may not be out of line. If the sample contains influenza B virus, the latex-labeled influenza B monoclonal antibody may be first bound by the influenza B virus in the sample. During the chromatography process, it may then be combined with the influenza B monoclonal antibody coated on the T3 area, and a colored line may appear in the T3 area.

If the sample does not contain MERS virus, the latex-labeled rabbit anti-MERS virus S1 protein polyclonal antibody may not be captured and bound by DPP4 coated on the T4 area during the chromatography, and the T4 area may not be out of line. If the sample contains MERS virus, the latex-labeled rabbit anti-MERS virus S1 protein polyclonal antibody may first be bound by the MERS virus in the sample. During the chromatography process, it may then be captured and bound to the DPP4 coated on the T4 area. A colored line may appear in the T4 area.

The control area (C) may be coated with goat anti-rabbit IgG polyclonal antibody, no matter whether there is novel coronavirus/IFVA/B/MERS-CoV in the sample, the latex labeled rabbit IgG may be bound by the goat anti-rabbit IgG polyclonal antibodies coated on the C area, and C lines may appear.

In some illustrative embodiments, upon completion of a test, the amount of latex-protein bound on the T line may be proportional to the concentration of novel coronavirus, IFV A, IFV B, or MERS-CoV in the sample, while the amount of latex on the control line C bound may be irrelevant to the amount of virus in the sample.

The advantages of the illustrative embodiments of the disclosure, in addition to the advantages of being fast, uncomplicated, inexpensive, stable, and also providing a test which can be carried out at home, based on the novel Coronavirus spike protein S1 ligand interacting with human ACE2 receptor, problems such as long monoclonal antibody development cycle and cross-reaction of antibodies are avoided, so as to improve the specificity of detection and quickly provide an effective kit. Embodiments may be suitable for detection of SARS-CoV-2 and all of its mutants. It has been found that this virus evolved into more contagious mutants through mutations in S1 proteins (such as D614G) that are stronger binding to ACE2 receptors. Thus, illustrative embodiments of the detection kit described herein based on ACE2 receptor may be more sensitive to such mutants. Using DPP4 receptor to detect the MERS-CoV, embodiments may also have good sensitivity and specificity, and may avoid cross reaction by using antibody detection. For the general public, it is difficult to distinguish influenza from COVID-19 and MERS. Therefore, it is beneficial to develop a kit, as described in illustrative embodiments herein, that it can test COVID-19, MERS, influenza A and B with one strip at the same time.

Illustrative embodiments of kits may include one or more strips, including dual strips in one test kit, as shown in FIG. 3. Strips may test for one or more viruses as shown herein, including but not limited to COVID-19, MERS, Influenza A, and Influenza B, including combinations thereof.

A novel coronavirus/MERS-CoV/influenza virus AB multiple rapid detection kit may be characterized in that the kit method may contain ACE2 protein labeled with color latex, and the preparation method of ACE2 protein labeled with color latex may include the following steps in some embodiments:

1) The c-terminal of the human ACE2 gene may be sequentially connected to AVI tag sequence and the 6×His tag to form an artificially designed sequence. The artificially designed sequence may be optimized by the host cell codon and then subcloned into a vector under its CMV promoter. A plasmid expressing ACE2-AVI tag-6×His tag fusion protein may be constructed, which is called ACE2 fusion protein plasmid.

2) Transfection of ACE2 fusion protein plasmid constructed in step 1) into a cell line, and a stable transfected cell line expressing ACE2 fusion protein may be established. Culture and expansion of the stable transfected cells, collected the supernatant which contained ACE2 fusion protein may further be performed.

3) ACE2 fusion protein may be obtained from the culture supernatant prepared in step 2) by protein purification column and ACE2 protein may be obtained. In some embodiments, the protein purification column may be an His tag affinity column, such as $Ni^{2+}$ or $Co^{2+}$ column.

4) The ACE2 protein obtained in step 3) may be site-directed biotinylated at its c-terminal by the biotin-protein ligase BirA. to obtain an ACE2-biotin.

5) Streptavidin SA may be coupled to color latex with carboxylic group, and obtained L-SA; ACE2-biotin obtained in step 4) may be co-incubated with L-SA thus obtaining L-SB-ACE2.

Further, a novel coronavirus/MERS-CoV/influenza virus AB multiple rapid detection kit may be characterized in that the kit method may contain DPP4 protein labeled with color latex, and the preparation method of DPP4 protein labeled with color latex may include the following steps in some embodiments:

1) The N-terminal of the human DPP4 gene may be sequentially connected to a rat growth hormone signal peptide, a 6×His tag and AVI tag sequence to form an artificially designed sequence. The artificially designed sequence may be optimized by the host cell codon and then subcloned into a vector under its CMV promoter. A plasmid expressing 6×His tag-AVI tag-DPP4 fusion protein may be constructed, which is called DPP4 fusion protein plasmid.

2) Transfection of DPP4 fusion protein plasmid constructed in step 1) into a cell line may occur, and a stable transfected cell line expressing DPP4 fusion protein may be established. The method may further include Culturing and expanding the stable transfected cells, and collecting the supernatant which may contain DPP4 fusion protein.

3) DPP4 fusion protein may be obtained from the culture supernatant prepared in step 2) by protein purification column and DPP4 protein may be obtained. Embodiments may include a protein purification column that is His tag affinity column, such as $Ni^{2+}$ or $Co^{2+}$ column.

4) The DPP4 protein obtained in step 3) may be site-directed biotinylated at its N-terminal by the biotin-protein ligase BirA. And the biotin-DPP4 may be obtained.

5) Streptavidin SA may be coupled to color latex with carboxylic group, obtained L-SA; DPP4-biotin obtained in step 4) may be co-incubated with L-SA, the L-SB-DPP4 may be obtained.

Further in some embodiments, a novel coronavirus/MERS-CoV/influenza virus A/B multiple rapid detection kit may be characterized that the human ACE2 gene is the extracellular part of human ACE2, that is the encoding gene sequence of part 1-739aa of GenBank: AB046569.1; the human DPP4 gene is the extracellular part of human DPP4, that is the encoding gene sequence of part 29-766aa of GenBank: KJ896722.1;the AVI tag sequence is GLNDIFEAQKIEWHE (SEQ ID NO: 5); codon may be optimized for human hosts; the vector may be lentivirus expression vector pCDH-CMV-MCS-EF1-copGFP; the plasmid of the constructed ACE2 fusion protein may is herein named pCDH-ACE2.copGFP; the plasmid of the constructed DPP4 fusion protein is herein named pCDH-DPP4.copGFP.

The artificially designed DNA sequence of ACE2 fusion protein is shown in SEQ ID NO: 1; its translated protein sequence is shown in SEQ ID NO: 2. See the accompanying sequence listing.

The artificially designed DNA sequence of DPP4 fusion protein is shown in SEQ ID NO: 3; its translated protein sequence is shown in SEQ ID NO: 4. See the accompanying sequence listing.

Further, a novel coronavirus/MERS-CoV/influenza virus A/B multiple rapid detection kit may be characterized that the cell lines for transfection can be HEK293 or CHO; the stable transfected cell line expressing ACE2 fusion protein is herein named ACE2.copGFP/293 or ACE2.copGFP/CHO; the stable transfected cell line expressing DPP4 fusion protein is herein named DPP4.copGFP/293 or DPP4.copGFP/CHO.

The establishment process of the stable transfected cell line may be: The pCDH-ACE2.copGFP or pCDH-DPP4.copGFP plasmid, pH1 plasmid and pH2 plasmid are co-transfected into lentivirus packaging cells 293V to prepare ACE2.copGFP or DPP4.copGFP lentivirus, and transfected HEK293 or CHO with ACE2.copGFP or DPP4.copGFP lentivirus.

Further, a novel coronavirus/MERS-CoV/influenza virus A/B multiple rapid detection kit may be characterized that the site-directed biotinylation may be performed at the end of the amino acid sequence SEQ ID NO:2 of ACE2 protein, the lysine(K) on the recognition site GLNDIFEAQKIEWHE (SEQ ID NO: 5) of biotin protein ligase; and the N-terminal of the amino acid sequence SEQ ID NO:4 of DPP4 protein, the lysine(K) on the recognition site GLNDIFEAQKIEWHE (SEQ ID NO: 5) of biotin protein ligase.

Further, a novel coronavirus/MERS-CoV/influenza virus A/B multiple rapid detection kit may be characterized that after the carboxyl color latex are activated with EDC/NHS crosslinker, streptavidin (SA) may be conjugated to the latex through peptide bonds to obtain L-SA; the ACE2-Biotin protein may be linked to L-SA by streptavidin-biotin reaction to obtain ACE2 protein labeled with color latex, named L-SB-ACE2; The same process may be followed to obtain L-SB-DPP4.

Further, a novel coronavirus/MERS-CoV/influenza virus A/B multiple rapid detection kit may have characteristics described in the kit that may also include using EDC/NHS crosslinking agent activated carboxyl colored latex, anti-Influenza A virus (IFVA) antibodies (capture), anti-Influenza B virus (IFVB) antibodies (capture) and rabbit IgG which may be respectively coupled to color latex by peptide bonds to obtain L-IFVA, L-IFVB and L-rabbit IgG.

Further, a novel coronavirus/MERS-CoV/influenza virus A/B multiple rapid detection kit may be characterized by the fact that the kit may also include 2 chromatography strips. The strip may include a bottom lining, nitrocellulose (NC) membrane, sample pad, release pad and absorbent paper. The sample pad, release pad, NC membrane and absorbent paper may be assembled on the bottom lining, in which the release pad and absorbent paper may be stacked on either end of the NC membrane, and the sample pad may be stacked on the release pad.

In one of the strips, L-IFVA,L-SB-ACE2 and L-rabbit IgG may be mixed and sprayed on the release pad of the strip; from its release pad to the absorbent paper, the test line area T1(Influenza A virus), T2(Novel Coronavirus),and control line area C1 may be set successively on the NC membrane. And they may be coated with anti-influenza A virus monoclonal antibody (detection type), anti-S1 protein of SARS-CoV-2 polyclonal antibodies, goat anti rabbit IgG polyclonal antibody (GAR) respectively. This strip may be named as strip A.

In the other strip, L-IFVB,L-SB-DPP4 and L-rabbit IgG may be mixed and sprayed on the release pad of the strip; from its release pad to the absorbent paper, the test line area T3(Influenza B virus), T4(MERS-CoV), and control line area C2 may be set successively on the NC membrane. And they may be coated with anti-influenza B virus monoclonal antibody (detection type), anti-S1 protein of MERS-CoV polyclonal antibodies, and goat anti rabbit IgG polyclonal antibody (GAR) respectively. This strip may be named as strip B.

In some embodiments, the test strips A and B may be assembled on a double strip card. A novel coronavirus, MERS and influenza A/B virus four-in-one rapid detection kit may be constructed. Among them, novel coronavirus and influenza A virus can be detected on strip A, while MERS and influenza B virus can be detected on strip B.

Further, a novel coronavirus/MERS-CoV/influenza virus A/B multiple rapid detection kit is characterized that, when testing, as long as two sample holes in the reagent plate are respectively sampled, within about 3-15 minutes, one may visually observe T1 of influenza A virus, T2 of novel Coronavirus, T3 of influenza B virus or T4 of MERS virus, which one is positive for the corresponding T line is appeared; if not, it is negative.

Further, a novel coronavirus/MERS-CoV/influenza virus AB multiple rapid detection kit may be characterized by the fact that the kit may be suitable for the detection of stool, urine, respiratory secretions, oral mucosal fluid, tear, and environmental samples. It can be applied to novel coronavirus, MERS-CoV, Influenza A and influenza B viruses for rapid detection, and identify the four viral epidemics simultaneously within about 3-15 minutes. It can be used for hospital testing, home testing, epidemiological investigation, and large-scale screening and diagnosis, and for global surveillance of coronavirus and influenza virus outbreaks.

In some illustrative embodiments, kits may be characterized by the fact that the strips of the kit were improved with biosafety, that is, RNAase was added to the sample pad or pads pretreatment solution to inhibit or inactivate the virus in the sample or samples. The concentration of RNAase in the sample pad pretreatment solution may be between about 0.1~1 U/ml.

Figure 4:
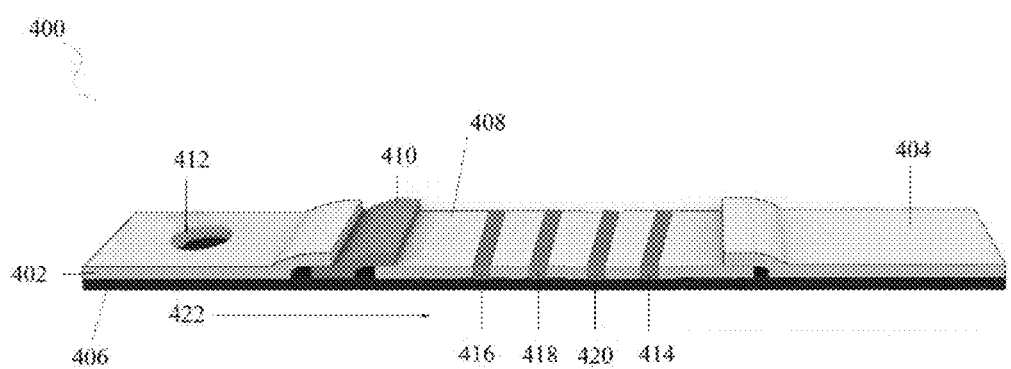
FIG. 4 depicts a sample test strip, according to embodiments described herein.

As shown in FIG. 4, illustrative embodiments may include a test strip 400, a sample pad 402, an absorbent paper 404, a bottom lining 406, a nitrocellulose membrane 408, a release pad 410. The sample pad 402, the release pad 410, the nitrocellulose membrane 408 and the absorbent paper 404 may be located on the bottom lining 406, as shown in FIG. 4. The release pad 410 and the absorbent paper 404 may further be located on opposing ends of the nitrocellulose membrane 408, each overlapping a respective end of the nitrocellulose membrane 408, and the sample pad 402 may be located on an end of the release pad 410, overlapping said end of the release pad 410, wherein said end of the release pad 410 is not on an end of the nitrocellulose membrane 408. In some illustrative embodiments, a sample may be placed into the kit through sample inlet 412. The sample may flow in a lateral flow direction, as shown by arrow 422.

In some illustrative embodiments, the test strip 400 further may comprise a first control line area 414 on the nitrocellulose membrane 408, a first test line area 416 on the nitrocellulose membrane 408, a second test line area 418 on the nitrocellulose membrane 408, and a third test line area 420 on the nitrocellulose membrane 408. Other embodiments, such as FIG. 3, may have more than one test strip within their kit, and may have more or less test line areas than as shown in FIGS. 3 and 4, including one or two test line areas. Each test strip in a kit may have a control line area. In some illustrative embodiments, the first test line area 416 may be located successively with the first control line area 414 wherein the first control line area 414 is located closer to the absorbent paper 404 as compared to the first test line area 416. The second test line area 418 may be located further from the absorbent paper 404 as compared to the first control line area 414. A positive test result for a virus would indicate a colored line in the respective test area, as taught herein, if such corresponded with a colored line in the first control line area 414.

Additional Specification Support

Embodiment 1. A novel coronavirus/MERS-CoV/influenza virus AB multiple rapid detection kit. It is characterized in that the kit method contains ACE2 protein labeled with color latex, and the preparation method of ACE2 protein labeled with color latex includes the following steps:
  1.1 The c-terminal of the human ACE2 gene was sequentially connected to AVI tag sequence and the 6×His tag to form an artificially designed sequence. The artificially designed sequence was optimized by the host cell codon and then subcloned into a vector under its CMV promoter. A plasmid expressing ACE2-AVI tag-6×His tag fusion protein was constructed, which is called ACE2 fusion protein plasmid.
  1.2 Transfection of ACE2 fusion protein plasmid constructed in step1.1 into a cell line, and a stable transfected cell line expressing ACE2 fusion protein was established. Cultured and expanded the stable transfected cells, collected the supernatant which contained ACE2 fusion protein.
  1.3 ACE2 fusion protein was obtained from the culture supernatant prepared in step1.2 by protein purification column that is His tag affinity column, such as Ni2+ or Co2+ column and ACE2 protein was obtained.
  1.4 The ACE2 protein obtained in step 1.3 was site-directed biotinylated at its c-terminal by the biotin-protein ligase BirA. And the ACE2-biotin was obtained
  1.5 Streptavidin SA was coupled to color latex with carboxylic group, obtained L-SA; ACE2-biotin obtained in step1.4 was co-incubated with L-SA, the L-SB-ACE2 was obtained.

Embodiment 2. A novel coronavirus/MERS-CoV/influenza virus AB multiple rapid detection kit. It is characterized in that the kit method contains DPP4 protein labeled with color latex, and the preparation method of DPP4 protein labeled with color latex includes the following steps:
  2.1 The N-terminal of the human DPP4 gene was sequentially connected to a rat growth hormone signal peptide, a 6×His tag and AVI tag sequence to form an artificially designed sequence. The artificially designed sequence was optimized by the host cell codon and then subcloned into a vector under its CMV promoter. A plasmid expressing 6×His tag-AVI tag-DPP4 fusion protein was constructed, which is called DPP4 fusion protein plasmid.
  2.2 Transfection of DPP4 fusion protein plasmid constructed in step 2.1 into a cell line, and a stable transfected cell line expressing DPP4 fusion protein was established. Cultured and expanded the stable transfected cells, collected the supernatant which contained DPP4 fusion protein.
  2.3 DPP4 fusion protein was obtained from the culture supernatant prepared in step 2.2 by protein purification column that is His tag affinity column, such as Ni2+ or Co2+ column and DPP4 protein was obtained.
  2.4 The DPP4 protein obtained in step 2.3 was site-directed biotinylated at its N-terminal by the biotin-protein ligase BirA. And the biotin-DPP4 was obtained
  2.5 Streptavidin SA was coupled to color latex with carboxylic group, obtained L-SA; biotin-DPP4 obtained in step 2.4 was co-incubated with L-SA, the L-SB-DPP4 was obtained.

Embodiment 3. As described in embodiment 1 and 2, a novel coronavirus/MERS-CoV/influenza virus A/B multiple rapid detection kit is characterized that the human ACE2 gene is the extracellular part of human ACE2, that is the encoding gene sequence of part 1-739aa of GenBank: AB046569.1; the human DPP4 gene is the extracellular part of human DPP4, that is the encoding gene sequence of part 29-766aa of GenBank: KJ896722.1;the AVI tag sequence is GLNDIFEAQKIEWHE (SEQ ID NO: 5); codon is optimized for human hosts; the vector is lentivirus expression vector pCDH-CMV-MCS-EF1-copGFP; the plasmid of the constructed ACE2 fusion protein was named pCDH-ACE2.copGFP; the plasmid of the constructed DPP4 fusion protein was named pCDH-DPP4.copGFP.

The artificially designed DNA sequence of ACE2 fusion protein is shown in SEQ ID NO: 1; its translated protein sequence is shown in SEQ ID NO: 2.

The artificially designed DNA sequence of DPP4 fusion protein is shown in SEQ ID NO: 3; its translated protein sequence is shown in SEQ ID NO: 4.

Embodiment 4. As described in embodiment 1 and 2, a novel coronavirus/MERS-CoV/influenza virus A/B multiple rapid detection kit is characterized that the cell lines for transfection can be HEK293 or CHO; the stable transfected cell line expressing ACE2 fusion protein was named ACE2.copGFP/293 or ACE2.copGFP/CHO; the stable transfected cell line expressing DPP4 fusion protein was named DPP4.copGFP/293 or DPP4.copGFP/CHO.

The establishment process of the stable transfected cell line was: the pCDH-ACE2.copGFP or pCDH-DPP4.copGFP plasmid, pH1 plasmid and pH2 plasmid were co-transfected into lentivirus packaging cells 293V to prepare ACE2.copGFP or DPP4.copGFP lentivirus, and transfected HEK293 or CHO with ACE2.copGFP or DPP4.copGFP lentivirus.

Embodiment 5. As described in embodiment 1 and 2, a novel coronavirus/MERS-CoV/influenza virus A/B multiple rapid detection kit is characterized that the site-directed biotinylation was performed at the end of the amino acid sequence SEQ ID NO:2 of ACE2 protein, the lysine(K) on the recognition site GLNDIFEAQKIEWHE (SEQ ID NO: 5) of biotin protein ligase; and the N-terminal of the amino acid sequence SEQ ID NO:4 of DPP4 protein, the lysine(K) on the recognition site GLNDIFEAQKIEWHE (SEQ ID NO: 5) of biotin protein ligase.

Embodiment 6. As described in embodiments 1 and 2, a novel coronavirus/MERS-CoV/influenza virus A/B multiple rapid detection kit is characterized that after the carboxyl color latex were activated with EDC/NHS crosslinker, streptavidin (SA) was conjugated to the latex through peptide bonds to obtain L-SA; the ACE2-Biotin protein was linked to L-SA by streptavidin-biotin reaction to obtain ACE2 protein labeled with color latex, named L-SB-ACE2; same as L-SB-DPP4.

Embodiment 7. As described in embodiment 1, a novel coronavirus/MERS-CoV/influenza virus A/B multiple rapid detection kit, its characteristics is described in the kit also includes using EDC/NHS crosslinking agent activated carboxyl colored latex, the anti-Influenza A virus (IFVA) antibodies (capture), anti-Influenza B virus (IFVB) antibodies (capture) and rabbit IgG were respectively coupled to color latex by peptide bonds to obtain L-IFVA, L-IFVB and L-rabbit IgG.

Embodiment 8. As described in embodiment 1, a novel coronavirus/MERS-CoV/influenza virus A/B multiple rapid detection kit is characterized by the fact that the kit also includes 2 chromatography strips. The strip includes bottom lining, nitrocellulose (NC) membrane, sample pad, release pad and absorbent paper. The sample pad, release pad, NC membrane and absorbent paper are assembled on the bottom lining, in which the release pad and absorbent paper are stacked on either end of the NC membrane, the sample pad is stacked on the release pad.

In one illustrative strip, L-IFVA,L-SB-ACE2 and L-rabbit IgG were mixed and sprayed on the release pad of the strip: from its release pad to the absorbent paper, the test line area T1(Influenza A virus), T2(Novel Coronavirus), and control line area C1 are set successively on the NC membrane. And they were coated with anti-influenza A virus monoclonal antibody (detection type), anti-S1 protein of SARS-CoV-2 polyclonal antibodies, goat anti rabbit IgG polyclonal antibody (GAR) respectively. This strip is named as strip A.

In another illustrative strip, L-IFVB,L-SB-DPP4 and L-rabbit IgG were mixed and sprayed on the release pad of the strip; from its release pad to the absorbent paper, the test line area T3(Influenza B virus), T4(MERS-CoV),and control line area C2 are set successively on the NC membrane. And they were coated with anti-influenza B virus monoclonal antibody (detection type), anti-S1 protein of MERS-CoV polyclonal antibodies, goat anti rabbit IgG polyclonal antibody (GAR) respectively. This strip is named as strip B.

The test strips A and B are assembled on a double strip card. A novel coronavirus, MERS and influenza A/B virus four-in-one rapid detection kit was constructed. Among them, novel coronavirus and influenza A virus can be detected on strip A, while MERS and influenza B virus can be detected on strip B.

Embodiment 9. As described in embodiment 8, a novel coronavirus/MERS-CoV/influenza virus A/B multiple rapid detection kit is characterized that, when testing, as long as the two sample holes in the reagent plate are respectively sampled, within about 3-15 minutes, visually observe T1 of influenza A virus, T2 of novel Coronavirus, T3 of influenza B virus or T4 of MERS virus, which one is positive for the corresponding T line is appeared; if not, it is negative.

Embodiment 10. As described in embodiment 8, a novel coronavirus/MERS-CoV/influenza virus A/B multiple rapid detection kit is characterized by the fact that the kit is suitable for the detection of stool, urine, respiratory secretions, oral mucosal fluid, tear, and environmental samples. It can be applied to novel coronavirus, MERS-CoV, Influenza A and influenza B viruses for rapid detection, and identify the four viral epidemics simultaneously within about 3-15 minutes. It can be used for hospital testing, home testing, epidemiological investigation, and large-scale screening and diagnosis, and for global surveillance of coronavirus and influenza virus outbreaks.

Reference will now be made to specific cases. These are illustrative embodiments and are not meant to be limited to their specific elements, but embodiments of the disclosure may include more or less as taught herein.

Illustrative Cases

The illustrative embodiments are further described below in combination with specific illustrative embodiments, provided that the scope of protection of the illustrative embodiments is not limited to this.

Case 1 Construction of Plasmid pCDH-ACE2.copGFP

The c-terminal of the human ACE2 gene, the encoding gene sequence of part 1-739aa of GenBank: AB046569.1, was sequentially connected to biotinylation tag sequence (GLNDIFEAQKIEWHE)(SEQ ID NO: 5), and 6xHis tag to form an artificially designed sequence. The artificially designed sequence was optimized by the host cell codon and then subcloned into a vector under its CMV promoter. A plasmid expressing ACE2-AVI tag-6xHis fusion protein was constructed, which is called ACE2 fusion protein plasmid. The artificially designed DNA sequence is shown in SEQ ID NO: 1; its expressed amino acid sequence is shown in SEQ ID NO:2. After the gene was synthesized, it was cloned into pCDH-CMV-MCS-EFI-CopGFP vector through ligase restriction sites EcoR I and Not I. The constructed plasmid is named pCDH-ACE2.copGFP (as shown in FIG. 1).

Figure 2:
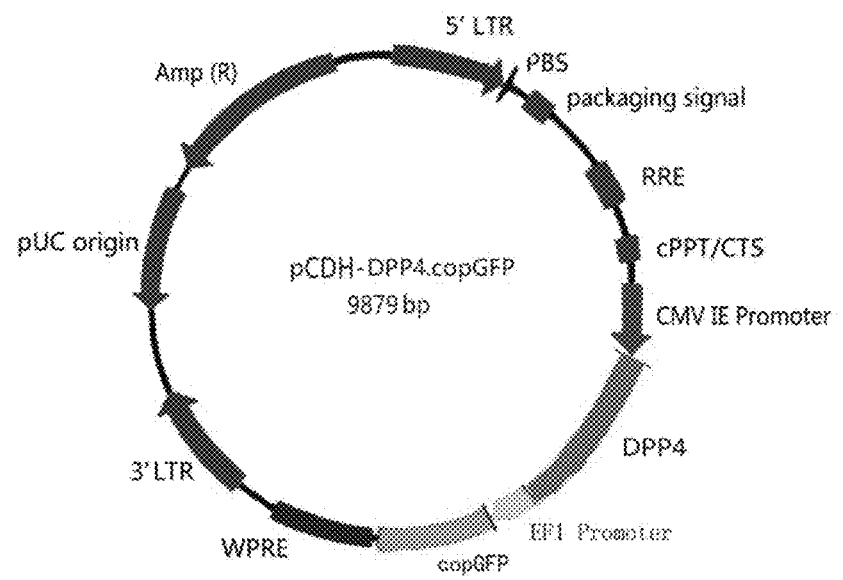
FIG. 2 is a plasmid map of pCDH-DPP4.copGFP.

The specific sequence of SEQ ID NO: 1 is shown in FIG. 2. In each of its end, EcoRI(GAATTC)/NotI(GCGGCCGC) is for gene subcloning; The part of 7-2223bp sequence encodes the extracellular domain (1-739aa) of human ACE2 protein; The part of 2224-2295bp sequence encodes the identification site of BirA enzyme(the first underlined part in FIG. 2); 2296-2314bp is the gene sequence of purified tag 6×His.

The specific sequence of SEQ ID NO:2 is shown in FIG. 3. The part of 1-739aa is human ACE2 protein extracellular domain; the part of 740-763aa is the BirA enzyme recognition site; 764-770aa is the purified tag 6×His.

Case 2 Construction of Plasmid pCDH-DPP4.copGFP

The N-terminal of the human DPP4 gene, the encoding gene sequence of part 29-766aa of GenBank: KJ896722.1, was sequentially connected to a rat growth hormone signal peptide(MAADSQTPWLLTFSLLCLLWPQEAGA), a 6xHis tag and AVI tag sequence (GLNDIFEAQKIEWHE (SEQ ID NO: 5)) to form an artificially designed sequence. The artificially designed sequence was optimized by the host cell codon and then subcloned into a vector under its CMV promoter. A plasmid expressing 6xHis-AVI tag-DPP4 fusion protein was constructed, which is called DPP4 fusion protein plasmid. The artificially designed DNA sequence is shown in SEQ ID NO: 3; its expressed amino acid sequence (the rat growth hormone signal peptide removed) is shown in SEQ ID NO:4. After the gene was synthesized, it was cloned into pCDH-CMV-MCS-EF1-CopGFP vector through ligase restriction sites EcoR I and Not I. The constructed plasmid is named pCDH-DPP4.copGFP (as shown in FIG. 2).

The specific sequence of SEQ ID NO: 3 is shown in the Sequence Listing Appendix. In each of its end, EcoRI (GAATTC)/NotI(GCGGCCGC) is for gene subcloning; The part of 7-84bp sequence encodes the rat growth hormone signal peptide; 85-102bp sequence encodes 6xHis tag; 103-147 bp sequence encodes AVI tag; 154-2367 bp sequence encodes extracellular domain (29-766aa) of human DPP4 protein.

The specific sequence of SEQ ID NO:4 is shown in the Sequence Listing Appendix.

Case 3 Establishment of ACE2.copGFP/293 Cell Line pCDH-ACE2.copGFP plasmid, pH1 plasmid and pH2 plasmid were co-transfected into lentivirus packaging line cells 293V to prepare ACE2.copGFP lentivirus and transfected into HEK293 cells. The ACE2. copGFP/293 stable cell line was established and cloned by picked up under a fluorescence microscope. The illustrative specific steps are as follows:

1) 293V Cells were seeded on five of 15 cm dishes the day before the experiment to ensure that the confluence of the cells reached 70%-80% before transfection.
2) 1-2h before transfection, the medium in dish was replaced with serum-free and antibiotic-free DMEM medium.
3) Prepare a 15 mL tube, add 5 mL 1xHBS, and then add 100 μg pCDH-ACE2.copGFP plasmid and 100 μg pH1/pH2 plasmid (pH1:pH2=3:1), and mixed gently.
4) Add 4 mL of PEI solution (10 μM), mix gently, and incubate at 37° C. for 20 min.
5) The transfection compound solution was divided into 5 equal parts and evenly added into five of 15 cm dishes to be transfected. The compound was distributed evenly by shaking gently.
6) After transfection for 6 h, the medium was replaced with DMEM complete medium (+10% FBS+1% penicillin/streptomycin).
7) The supernatant was collected after transfection at 48-72 h and centrifuged at 8000 g for 15 min. The supernatant was filtered by 0.45 μm membrane before centrifugation at 85000 g for 2 hours.
8) The supernatant was discarded, and the precipitate was resuspended with 0.5 mL complete medium (+10% FBS+1% penicillin/streptomycin) to infect HEK293 cells (12-well plate with 1 well, 60-70% confluence of cells).
10) The infected HEK293 cells were cultured for 2 days and subdivided into one 6-well plates with 6 Wells. The individual cells to be dispersed formed a clone cell mass (about 1 week), and the monoclonal cell mass with high expression of green fluorescent protein was picked out under a fluorescence microscope for amplification and cultured to establish ACE2. copGFP/293 stable cell line.

Case 4 Establishment of DPP4.copGFP/293 Cell Line pCDH-DPP4.copGFP plasmid, pH1 plasmid and pH2 plasmid were co-transfected into lentivirus packaging line cells 293V to prepare DPP4.copGFP lentivirus and transfected into HEK293 cells. The DPP4. copGFP/293 stable cell line was established and cloned by picked up under a fluorescence microscope. The specific steps are as same as Case 3.

Case 5 Preparation of ACE2-Biotin Protein

ACE2.copGFP/293 stable cells were cultured using protein-free 293 cell culture medium, and the supernatant was collected. ACE2 fusion protein was purified by $Ni^{2+}$-agarose.ACE2-biotin was obtained by binding biotin to the site (GLNDIFEAQKIEWHE (SEQ ID NO: 5)) of ACE2 by biotin protein ligase. The specific steps are as follows:

1) ACE2.copGFP/293 cells were expanded to cultured at a five-layer cell plant with HektorHEK293 protein or polypeptide-free cell medium.
2) The culture medium was collected and centrifuged at 12000 g for 30 min at 4° C. The supernatant was flowed through the $Ni^{2+}$-agarose column, the target protein is adsorbed; after washed with washing buffer (20 mM Tris-HCl, 150 mM NaCl, pH8.0), add eluent buffer(200 mM imidazole, 20 mM Tris-HCl,150 mM NaCl, pH8.0) to collect the eluent.
3) ACE2 protein was concentrated in the ultrafiltration tube with the molecular weight trapped by 10KD protein and replaced with BirA enzyme connecting buffer (10 mM ATP, 10 mM MgOAc, 50 μM-biotin). According to the product instructions, BirA enzyme was used to site-point biotinylation of ACE2 protein, which was connected to lysine (K) in the GLNDIFEAQKIEWHE (SEQ ID NO: 5) sequence to obtain ACE2-biotin.

Case 6 Preparation of Biotin-DPP4 Protein

DPP4.copGFP/293 stable cells were cultured using protein-free 293 cell culture medium, and the supernatant was collected. DPP4 fusion protein was purified by $Ni^{2+}$-agarose. biotin-DPP4 was obtained by binding biotin to the site (GLNDIFEAQKIEWHE (SEQ ID NO: 5)) of DPP4 by biotin protein ligase. The specific illustrative steps are as same as Case 5.

Case 7 Preparation of L-SB-ACE2, L-SB-DPP4 L-IFVA, L-IFVB and L-Rabbit IgG

By coupling streptavidin (SA) to carboxylic color latex, ACE2-biotin can be firmly labeled with color latex through the SA-biotin system. This method not only avoids ACE2 or DPP4 protein functional inactivation caused by ACE2 or DPP4 directly through —NH4 and —COOH condensation reaction, but also forms multistage amplification of detection signals. The specific illustrative steps are as follows:

1) Conjugate streptavidin (SA) to carboxyl color latex according to the method in the product manual to obtain L-SA.
2) Rabbit IgG was also coupled to carboxylic color latex to obtain L-Rabbit IgG for use in the control system of the strips.
3) Anti-IFVA monoclonal antibody (Capture) was coupled to carboxylic color latex to obtain L-IFVA.
4) Anti-IFVB monoclonal antibody (Capture) was coupled to carboxylic color latex to obtain L-IFVB
5) L-SA and ACE2-biotin were mixed in PBS buffer at pH7.4 at a molar ratio of 1:4 (L-SA was calculated as labeled SA) and incubated at 37° C. at 150 rpm for 1 hour to obtain L-SB-ACE2.
6) L-SA and biotin-DPP4 were mixed in PBS buffer at pH7.4 at a molar ratio of 1:4 (L-SA was calculated as labeled SA) and incubated at 37° C. at 150 rpm for 1 hour to obtain L-SB-DPP4.

7) Centrifuge at 15000 g at 4° C. for 30 minutes, remove the supernatant, and the precipitate was resuspended with PB buffer (pH7.0, 1% BSA, 8% sucrose, 0.05% NaN₃).

Case 8 Preparation of Novel Coronavirus/HERS-CoV/Influenza Virus A/B Multiple Rapid Detection Kit In this case, a novel coronavirus/MERS-CoV/influenza virus AB multiple rapid detection kit (latex method) was prepared, and established a biosafety system for virus inactivation.

1) 0.2 U/ml of nuclease were added to the sample pad pretreatment solution. Coronaviruses are RNA viruses, so nuclease inhibit or inactivate the virus by degrading its nucleic acid. The sample pad pretreatment solution was Tris buffer solution containing 0.5% tween-20 at pH7.4.

2) L-SB-ACE2, L-IFVA, and L-Rabbit IgG prepared in Case 7 above were mixed and sprayed on the release pad of the kit, dried at 37° C. for 12h for standby use, named release pad A.

3) L-SB-DPP4, L-IFVB, and L-Rabbit IgG prepared in Case 7 above were mixed and sprayed on the release pad of the kit, dried at 37° C. for 12h for standby use, named release pad B.

4) The anti-IFVA monoclonal antibody (detection), rabbit anti-S1 protein of Novel SARS-CoV-2 polyclonal antibodies, and goat anti-rabbit IgG polyclonal antibody (GAR) were diluted to about 0.5 mg/mL with coated diluent (150 mM PB, pH 7.4), and was sprayed evenly on the test lines T1,T2, and control line (C1) of the cellulose nitrate membrane, respectively. Dried at 37° C. for 12 h, and sealed the bag for later use, named as NC membrane A.

5) The anti-IFVB monoclonal antibody (detection), rabbit anti-S1 protein of MERS-CoV polyclonal antibodies, and goat anti-rabbit IgG polyclonal antibody(GAR) were diluted to about 0.5 mg/mL with coated diluent (150 mM PB, pH 7.4), and was sprayed evenly on the test lines T3,T4, and control line (C2) of the cellulose nitrate membrane, respectively. Dried at about 37° C. for about 12 h, and sealed the bag for later use, named as NC membrane B.

6) The sample pad, release pad, nitrocellulose film and absorbent paper were lap assembled on the bottom lining. The release pad and absorbent paper were stacked on each end of the nitrocellulose membranes respectively. The sample pad is stacked on the release pad and assembled to form a test board. Two kind of test boards were made: board A, release pad A was combined with NC membrane A; test B, release pad B was combined with NC membrane B. The test boards were cut into about 3.78 mm strips and two kind of test strips were made: strip A and strip B. Assembled strip A and strip B in a double strips card to prepare into the novel coronavirus/MERS-CoV/influenza virus A/B multiple rapid detection kit.

Case 9 Application of the Novel Coronavirus/MRS-CoV/Influenza Virus A/B Multiple Rapid Detection Kit The novel coronavirus/MERS-CoV/influenza virus A/B multiple rapid detection kit can be applied to the rapid detection of SARS-CoV-2 (including its variants), A/B influenza virus. It is suitable for the detection of various biological and environmental samples including stool, urine, sputum, tear, oral mucosal fluid, respiratory secretion, whole blood, plasma, serum.

1) Novel Coronavirus sensitivity test experiment: Recombinant S1 protein of SARS-CoV-2, purchased from Sino Biological Inc., was formulated into 1 nM, 5 nM, 15 nM, 20 nM with PBS (pH7.4), and PBS (pH7.4) as blank group, each concentration group is set up with 5 replicates, and this kit is used for measurement. The T2 line was observed by naked eye about 10-15 minutes after chromatography with about 100 μl of sample added per well. The results showed that the T2 lines had no color development and were negative at blank, 1 and 5 nM concentrations of S1 protein samples; while the T2 lines showed color lines from weak to strong at 10, 15 and 20 nM concentrations of S1 protein samples, all of which were positive. It is explained that the sensitivity of the test strip to S1 protein of SARS-CoV-2 is up to about 10 nM.

2) Novel Coronavirus cross-reactivity test experiment: A cross-reaction test is carried out for other common infectious disease pathogens by using the product. Three groups of parallel control experiments were conducted on samples of human epidemic coronavirus (HKU1, OC43, NL63 and 229E), influenza, common virus and Mycoplasma Pneumoniae, respectively. After data analysis, the product did not cross-reaction with them.

In theory, it does not cross-reactivity with coronaviruses infected with other receptors (such as DPP4 of MERS). SARS also use ACE2 receptor, but the affinity is 1/10-1/20 lower than SARS-CoV-2, so there may be taking weak cross-reaction.

The recombinant S1 proteins of SARS-CoV-2 SARS-CoV, HCoV-NL63, MERS-CoV, HCoV-229E, HCoV-HKU1, HCoV-OC43, G Protein of Human RSV (B1), HA protein of Influenza A H1N1, Influenza B were taken and prepared with PBS to form 0.00, 1.56, 3.13, 6.25, 12.50, and 25.00 μg/ml each. Took 100 μl each and added it to the strip. After 15 minutes, the T2 results showed that SARS-CoV-2 was strong positive, SARS-CoV was weak positive, and all others were negative (see Table 1).

TABLE 1

Cross-reactivity test of novel coronavirus/MERS-CoV/influenza virus A/B multiple rapid detection kit (the result of SARS-CoV-2 test line, T2)

| Concentration of Recombinant Proteins (μg/ml) | 0.00 | 1.56 | 3.13 | 6.25 | 12.50 | 25.00 |
|---|---|---|---|---|---|---|
| SARS-CoV-2 S1 Protein | − | − | + | + | ++ | +++ |
| SARS-CoV S1 Protein | − | − | − | − | − | + |
| HCoV-NL63 S1 Protein | − | − | − | − | − | − |
| MERS-CoV S1 Protein | − | − | − | − | − | − |
| HCoV-229E S1 Protein | − | − | − | − | − | − |
| HCoV-HKU1 S1 Protein | − | − | − | − | − | − |
| MERS-CoV S1 Protein | − | − | − | − | − | − |
| Human RSV (B1) G Protein | − | − | − | − | − | − |
| Influenza A H1N1 HA Protein | − | − | − | − | − | − |
| Influenza B HA Protein | − | − | − | − | − | − |

Because ACE2 receptor protein was used to detect novel coronavirus, there should be no cross-reaction against other viruses except those viruses with ACE2 receptor as the infection mechanism. However, illustratively, S1 from novel coronavirus is the strongest ligand protein known to bind ACE2 receptor protein, Kd≈15 nM. The second is S1 of SARS-CoV, Kd≈156 nM, so a weak cross-reaction may occur. The experimental results are consistent with the theoretical expectations.

1) MERS-CoV sensitivity test experiment: Recombinant S1 protein of MERS-CoV, purchased from Sino Biological Inc., was formulated into 1 nM, 5 nM, 15 nM, 20 nM with PBS (pH7.4), and PBS (pH7.4) as blank group, each concentration group is set up with 5 replicates, and this kit is used for measurement. The T4 line was observed by naked eye 10-15 minutes after chromatography with 100 µl of sample added per well. The results showed that the T4 lines had no color development and were negative at blank, about 1 and about 5 nM concentrations of MERS-CoV S1 protein samples; while the T4 lines showed color lines from weak to strong at about 10, about 15 and about 20 nM concentrations of MERS-CoV S1 protein samples, all of which were positive. It is explained that the sensitivity of the test strip to S1 protein of MERS-CoV is up to about 10 nM.

2) Novel Coronavirus cross-reactivity test experiment: A cross-reaction test is carried out for other common infectious disease pathogens by using the product. Three groups of parallel control experiments were conducted on samples of human epidemic coronavirus (HKU1, OC43, NL63 and 229E), influenza, common virus and Mycoplasma Pneumoniae, respectively. After data analysis, the product did not cross-reaction with them.

In theory, it does not cross-reactivity with coronaviruses infected with other receptors (such as ACE2 of SARS-CoV-2).

The recombinant S1 proteins of SARS-CoV-2, SARS-CoV, HCoV-NL63, MERS-CoV, HCoV-229E, HCoV-HKU1, HCoV-OC43, G Protein of Human RSV (B1), HA protein of Influenza A H1N1, Influenza B were taken and prepared with PBS to form 0.00, 1.56, 3.13, 6.25, 12.50, and 25.00 µg/ml each. Took 100 µl each and added it to the strip. After 15 minutes, the T4 results showed that SARS-CoV-2 was strong positive, SARS-CoV was weak positive, and all others were negative (see Table 2).

TABLE 2

Cross-reactivity test of novel coronavirus/MERS-CoV/
influenza virus A/B multiple rapid detection kit
(the result of MERS-CoV test line, T4)

| Concentration of Recombinant Proteins (µg/ml) | 0.00 | 1.56 | 3.13 | 6.25 | 12.50 | 25.00 |
|---|---|---|---|---|---|---|
| MERS-CoV S1 Protein | − | − | + | + | ++ | +++ |
| SARS-CoV-2 S1 Protein | − | − | − | − | − | − |
| SARS-CoV S1 Protein | − | − | − | − | − | − |
| HCoV-NL63 S1 Protein | − | − | − | − | − | − |
| MERS-CoV S1 Protein | − | − | − | − | − | − |
| HCoV-229E S1 Protein | − | − | − | − | − | − |
| HCoV-HKU1 S1 Protein | − | − | − | − | − | − |
| Human RSV (B1) G Protein | − | − | − | − | − | − |
| Influenza A H1N1 HA Protein | − | − | − | − | − | − |
| Influenza BHA Protein | − | − | − | − | − | − |

1) Quality evaluation and control of influenza A/B virus antigen detection reagent:

National Standard for Influenza A/B Viral Antigens Detection Kit (Table 3) was used for quality evaluation and control of Influenza A/B virus antigen Detection Kit.

(1) Coincidence rate of positive reference: PC01-PC04 influenza B virus was positive and Influenza A virus was negative. PC05-PC10 influenza A virus was positive and Influenza B virus was negative.

(2) Coincidence rate of negative reference: NC01-NC06- Both influenza A and B viruses were negative.

(3) Repeatability: CV1 and CV2 were repeated for 10 times each, CV1 was positive for influenza A virus and negative for influenza B virus, while CV2 was positive for influenza B virus and negative for influenza A virus; the reaction The results were consistent and the chroma was uniform.

TABLE 3

Composition and properties of national reference
reagent for influenza A/B virus antigen detection

| Reference types | Serial Number | Types of Pathogens |
|---|---|---|
| Positive reference | PC01 | B/Victoria |
| | PC02 | B/Victoria |
| | PC03 | B/Yamagata |
| | PC04 | B/Yamagata |
| | PC05 | A type of H1N1 |
| | PC06 | A type of H1N1 |
| | PC07 | Seasonal H1N1 |
| | PC08 | Seasonal H3N2 |
| | PC09 | Seasonal H3N2 |
| | PC10 | A type of H7N9 |
| Negative reference | NC01 | Measles virus |
| | NC02 | Mumps virus |
| | NC03 | Rubella virus |
| | NC04 | Chicken pox - Herpes zoster virus |
| | NC05 | *Staphylococcus aureus* |
| | NC06 | *Pseudomonas aeruginosa* |
| Repeatable reference | CV1 | Seasonal H3N2 |
| | CV2 | B/Victoria |
| Minimum inspection limit reference items | S1 | A type of H1N1 |
| | S2 | Seasonal H1N1 |
| | S3 | B/Victoria |
| | S4 | B/Yamagata |
| | S5 | Seasonal H3N2 |

(4) Limit of detection:

S1: The titer is not higher than $1.22 \times 10^4$ TCID$_{50}$/L(1:80 dilution), the results were positive for influenza A virus and negative for influenza B virus.

S2: The titer is not higher than $3.25 \times 10^4$ TCID$_{50}$/L(1:40 dilution), the results were positive for influenza A virus and negative for influenza B virus.

S3: The titer is not higher than $5.25 \times 10^5$ TCID$_{50}$/L(1:40 dilution), the results were positive for influenza B virus and negative for influenza A virus.

S4: The titer is not higher than $1.00 \times 10^4$ TCID$_{50}$/L(1:10 dilution), the results were positive for influenza B virus and negative for influenza A virus.

S5: The titer is not higher than $1.25 \times 10^3$ TCID$_{50}$/L(1:80 dilution), the results were positive for influenza A virus and negative for influenza B virus.

While the illustrative embodiments described above detail kits that test for coronavirus/MERS-CoV/influenza virus A/B, the teachings herein may also test for kits that use one, two, or three of these viruses using the principles taught herein. Test kits may have one or two test strips and may have one or more control lines for said test strips. Embodiments as described herein may include, for example, a test kit that teaches to three of the four listed viruses. A test kit that detects for two or one of the viruses is also envisioned by virtue of this disclosure.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of any single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in quantities, proportions, materials, and manner of making and use may be made without departing from the principles and concepts set forth herein.

What is claimed is:

1. A novel coronavirus/MERS-CoV/influenza virus A/B multiple rapid detection kit that comprises:
at least one test strip to receive a biological sample including:
at least one release pad, wherein the at least one release pad includes:
a latex-labeled ACE2 complex-sprayed on the at least one release pad, wherein the latex-labeled ACE2 complex is prepared using the following steps:
sequentially connecting a c-terminal of a human ACE2 gene to an AVI tag sequence and a 6xHis tag to form an artificially designed sequence, wherein the AVI tae sequence comprises GLN-DIFEAQKIEWHE (SEQ ID NO: 5);
optimizing the artificially designed sequence by a host cell codon;
subcloning the artificially designed sequence into a vector under a CMV promoter;
constructing a plasmid expressing a ACE2-AVI tag-6xHis tag fusion protein to obtain an ACE2 fusion protein plasmid;
transfecting the ACE2 fusion protein plasmid into a cell line;
establishing a stable transfected cell line expressing ACE2 fusion protein;
culturing and expanding the stable transfected cell line;
collecting a culture supernatant from the stable transfected cell line;
obtaining the ACE2 fusion protein from the culture supernatant with a protein purification column;
site-directed biotinylating the ACE2 fusion protein at a c-terminal by a biotin-protein ligase BirA to obtain an ACE2-biotin;
coupling a Streptavidin SA to a first color latex with a carboxylic group to obtain L-SA; and
co-incubating the ACE2-biotin with the L-SA to obtain a L-SB-ACE2;
a latex-labeled DPP4 complex sprayed on the at least one release pad, the latex-labeled DPP4 complex including a DPP4 protein labeled with a second color latex;
a latex-labeled anti-IFVA mAb complex (capture) sprayed on the at least one release pad, the latex-labeled anti-IFVA mAb complex (capture) including anti-influenza A virus monoclonal antibodies labeled with a third color latex;

a latex-labeled anti-IFVB mAb complex (capture) sprayed on the at least one release pad, the latex-labeled anti-IFVB mAb complex (capture) including anti-influenza B monoclonal antibodies labeled with a fourth color latex; and a first test area coated with an anti-S1 protein of SARS-CoV-2 polyclonal antibodies to capture SARS-CoV-2 from the biological sample and the latex-labeled ACE2 complex indicated by color latex agglutination;

a second test area coated with an anti-S1 protein of MERS-CoV polyclonal antibodies to capture MERS-CoV from the biological sample and the latex-labeled DPP4 complex indicated by color latex agglutination;

a third test area coated with an anti-influenza A virus monoclonal antibody (detection) to capture an influenza A virus from the biological sample and the latex-labeled anti-IFVA mAb complex (capture) indicated by color latex agglutination; and a fourth test area coated with an anti-influenza B virus monoclonal antibody (detection) to capture an influenza B virus from the biological sample and the latex-labeled anti-IFVB mAb complex (capture) indicated by color latex agglutination.

2. The kit of claim 1, wherein the protein purification column is a His tag affinity column including at least one of a Ni2+ column and a Co2+ column.

3. The kit of claim 1, wherein the vector is lentivirus expression vector pCDH-CMV-MCS-EF1-copGFP, wherein the ACE2 fusion protein plasmid is pCDH-ACE2.copGFP, wherein the artificially designed DNA sequence of ACE2 fusion protein is shown in SEQ ID NO: 1, and wherein a translated protein sequence is shown in SEQ ID NO: 2.

4. The kit of claim 1, wherein the cell lines comprise at least one of HEK293 and CHO, wherein the stable transfected cell line expressing ACE2 fusion protein comprises at least one of ACE2.copGFP/293 and ACE2.copGFP/CHO; wherein the establishment process of the stable transfected cell line comprises pCDH-ACE2.copGFP plasmid; wherein the step of transfecting further comprises co-transfecting pH1 plasmid and pH2 plasmid into lentivirus packaging cells 293V to prepare ACE2.copGFP lentivirus, and transfecting HEK293 or CHO with ACE2.copGFP lentivirus.

5. The kit of claim 1, wherein the step of biotinylating the ACE2 fusion protein further comprises site-directed biotinylating at an end of an amino acid sequence SEQ ID NO:2 of ACE2 protein, the lysine(K) on the recognition site GLNDIFEAQKIEWHE (SEQ ID NO: 5) of biotin protein ligase.

6. The kit of claim 1, wherein the method of preparing the ACE2 protein further comprises:
activating a carboxyl color latex with an EDC/NHS crosslinker;
conjugating streptavidin (SA) to the carboxyl color latex through peptide bonds to obtain an L-SA; and
linking the ACE2-Biotin protein to the L-SA by a streptavidin-biotin reaction to obtain an ACE2 protein labeled with color latex.

7. The kit of claim 1, wherein the biological sample includes at least one of: stool, urine, respiratory secretions, oral mucosal fluid, and a tear.

8. The kit of claim 1, wherein a time frame to observe whether the biological sample applied to the at least one test strip tests positive for a virus is in a range of about 3 and about 15 minutes.

9. The kit of claim 1, wherein a positive test result for a specific virus is indicated by a colored line appearing on a test line in a test area designated for the specific virus and a colored line appearing on a test control line area.

10. The kit of claim 1, wherein the DPP4 protein labeled with color latex preparation method comprises the following steps:
sequentially connecting an N-terminal of a human DPP4 gene to a rat growth hormone signal peptide, a 6xHis tag and AVI tag sequence to form an artificially designed sequence;
optimizing the artificially designed sequence using a host cell codon;
subcloning the artificially designed sequence into a vector under a CMV promoter;
constructing a plasmid expressing 6xHis tag-AVI tag-DPP4 fusion protein which is called DPP4 fusion protein plasmid;
transfecting the DPP4 fusion protein plasmid into a cell line;
establishing a stable transfected cell line expressing DPP4 fusion protein;
culturing and expanding the stable transfected cell line;
collecting a culture supernatant from the stable transfected cell line;
obtaining the DPP4 fusion protein from the culture supernatant by a protein purification column;
site-directed biotinylating the DPP4 fusion protein at an N-terminal by a biotin-protein ligase BirA to obtain a biotin-DPP4;
coupling a Streptavidin SA to color latex with carboxylic group, to obtain a L-SA; and
co-incubating a biotin-DPP4 with the L-SA, to obtain L-SB-DPP4.

11. The kit of claim 10, wherein the DPP4 fusion protein plasmid is pCDH-DPP4.copGFP.

12. The kit of claim 10, wherein the artificially designed DNA sequence is shown in SEQ ID NO: 3, and wherein a translated protein sequence is shown in SEQ ID NO: 4.

13. The kit of claim 10, wherein the stable transfected cell line expressing DPP4 fusion protein comprises at least one of DPP4.copGFP/293 and DPP4.copGFP/CHO, wherein the stable transfected cell line comprises pCDH-DPP4.copGFP plasmid, wherein the step of transfecting further comprises co-transfecting pH1 plasmid and pH2 plasmid into lentivirus packaging cells 293V to prepare DPP4.copGFP lentivirus and transfecting HEK293 or CHO with DPP4.copGFP lentivirus.

14. The kit of claim 10, wherein the step of biotinylating the ACE2 fusion protein further comprises site-directed biotinylating an N-terminal of the amino acid sequence SEQ ID NO:4 of DPP4 protein, the lysine(K) on the recognition site GLNDIFEAQKIEWHE (SEQ ID NO: 5) of biotin protein ligase.

15. The kit of claim 1, wherein the at least one test strip comprises:
a bottom lining;
at least one nitrocellulose membrane to house the first test area, the second test area, the third test area, and the fourth test area;
a sample pad, and
an absorbent paper,
wherein the sample pad, the release pad, the nitrocellulose membrane and the absorbent paper are located on the bottom lining,
wherein the release pad and the absorbent paper are further located on opposing ends of the nitrocellulose membrane, each overlapping a respective end of the nitrocellulose membrane, and wherein the sample pad is located on an end of the release pad, overlapping the end of the release pad, wherein the end of the release pad is not on an end of the nitrocellulose membrane.

16. The kit of claim 1, wherein the release pad further comprises:
   an L-rabbit IgG; and
   the kit further comprises at least one control line area on a nitrocellulose membrane,
   wherein the at least one control line area comprises goat anti-rabbit IgG polyclonal antibody.

17. The kit of claim 1, wherein the kit includes two test strips, each test strip including a respective release pad, the first release pad including:
   an L-IFVA,
   an L-SB-ACE2, and
   an L-rabbit IgG; and
   the second release pad including:
   an L-IFVB,
   an L-SB-DPP4, and
   an L-rabbit IgG, and
   the kit further comprising:
   a first control line area, a first test line area, and a second test line area located on a first nitrocellulose membrane;
   a second control line area,
   a third test line area, and
   a fourth test line area located on a second-nitrocellulose membrane,
   wherein the first test line area is located successively with the first control line area wherein the first control line area is located closer to an absorbent paper as compared to the first test line area,
   wherein the second test line area is located further from the absorbent paper as compared to the first control line area,
   wherein the third test line area is located successively with the second control line area wherein the second control line area is located closer to the absorbent paper as compared to the third test line area,
   wherein the fourth test line area is located further from the absorbent paper as compared to the second control line area,
   wherein the first test line comprises a coating of anti-Influenza A virus monoclonal antibody, the second test line area comprises a coating of anti-S1 protein of SARS-CoV-2 polyclonal antibodies, the third test line comprises a coating of anti-Influenza B virus monoclonal antibody, the fourth test line area comprises a coating of anti-S1 protein of MERS-CoV polyclonal antibodies, and
   the first control line area and the second control line area comprise goat anti rabbit IgG polyclonal antibody.

18. The kit of claim 1, wherein the kit further comprises a double strip card wherein a first strip of the double strip card is configured to detect two of novel coronavirus, influenza A virus, MERS, and influenza B virus, and wherein a second strip of the double strip card is configured to detect a remaining two of novel coronavirus, influenza A virus, MERS and influenza B virus.

19. The kit of claim 15, wherein the kit includes two test strips, wherein each test strip includes one sample well in the sample pad, one control line area, and two test line areas, and wherein each test line area detects a presence of a specific virus.

20. The kit of claim 15, further comprising a control area coated with goat anti-rabbit IgG polyclonal antibody to bind latex labeled rabbit IgG when at least one of a novel coronavirus, MERS-CoV, IFVA, and IFVB are present in the biological sample indicated by color latex agglutination.

21. The kit of claim 1, wherein a negative test result for a specific virus is indicated by no line appearing on a test line in a test area designated for the specific virus and a colored line appearing on a test control line area.

* * * * *